(12) United States Patent
Medlock et al.

(10) Patent No.: US 10,059,738 B2
(45) Date of Patent: Aug. 28, 2018

(54) PROCESS FOR THE PRODUCTION OF A DIPEPTIDE DERIVATIVE

(71) Applicant: DSM IP Assets B.V., Heerlen (NL)

(72) Inventors: Jonathan Alan Medlock, Kaiseraugst (CH); Peter Wikstroem, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 57 days.

(21) Appl. No.: 15/321,792

(22) PCT Filed: Jun. 1, 2015

(86) PCT No.: PCT/EP2015/062098
§ 371 (c)(1),
(2) Date: Dec. 23, 2016

(87) PCT Pub. No.: WO2015/197309
PCT Pub. Date: Dec. 30, 2015

(65) Prior Publication Data
US 2017/0145054 A1    May 25, 2017

(30) Foreign Application Priority Data
Jun. 25, 2014  (EP) ..................................... 14173859

(51) Int. Cl.
*C07C 231/14*  (2006.01)
*C07K 5/062*  (2006.01)
*C07K 1/02*  (2006.01)
*C07K 1/06*  (2006.01)
*C07K 1/107*  (2006.01)
*C07K 1/10*  (2006.01)

(52) U.S. Cl.
CPC ............ *C07K 5/06069* (2013.01); *C07K 1/02* (2013.01); *C07K 1/061* (2013.01); *C07K 1/10* (2013.01); *C07K 1/1075* (2013.01)

(58) Field of Classification Search
None
See application file for complete search history.

(56) References Cited

U.S. PATENT DOCUMENTS

2002/0037857 A1    3/2002 Semple et al.

FOREIGN PATENT DOCUMENTS

EP     1 483 285        12/2004
WO     WO 03/076457     9/2003

OTHER PUBLICATIONS

Kunzel et al. (Bioorganic and Medicinal Chemistry Letters, 2002, 12, 645).*
International Search Report for PCT/EP2015/062098 dated Sep. 15, 2015, 3 pages.

* cited by examiner

*Primary Examiner* — Sudhakar Katakam
*Assistant Examiner* — Jennifer Sawyer
(74) *Attorney, Agent, or Firm* — Nixon & Vanderhye P.C.

(57) ABSTRACT

The present invention is related to a novel and improved process for the manufacture of compounds of formula (I) or salts thereof herein designated as benzylsulfonyl-Ser-X-4-amidinobenzylamide, wherein R is a $C_1$ to $C_6$ linear or branched aliphatic hydrocarbon chain optionally substituted with a $C_6$ to $C_{10}$ aromatic group.

16 Claims, No Drawings

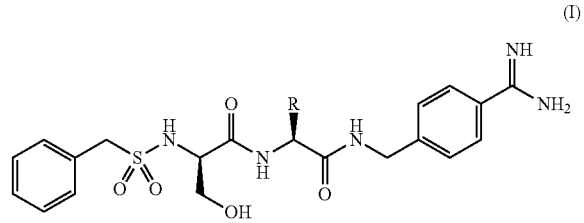
(I)

PROCESS FOR THE PRODUCTION OF A DIPEPTIDE DERIVATIVE

This application is the U.S. national phase of International Application No. PCT/EP2015/062098 filed Jun. 1, 2015 which designated the U.S. and claims priority to EP Patent Application No. 14173859.1 filed Jun. 25, 2014, the entire contents of each of which are hereby incorporated by reference.

BRIEF DESCRIPTION OF THE INVENTION

The present invention is related to a novel and improved process for the manufacture of compounds of formula (I) or salts thereof herein designated as benzylsulfonyl-Ser-X-4-amidinobenzylamide.

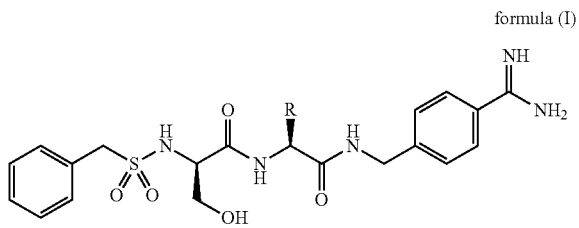

formula (I)

wherein R is a $C_1$ to $C_6$ linear or branched aliphatic hydrocarbon chain optionally substituted with a $C_6$ to $C_{10}$ aromatic group.

BACKGROUND OF THE INVENTION

Benzylsulfonyl dipeptide derivatives such as for example benzylsulfonyl-D-Ser-L-homoPhe-(4-amidino-benzylamide) have previously been described as potent urokinase inhibitors (WO2009/026949). Urokinase (uPA), also called urokinase-type plasminogen activator, is a multidomain serine protease (EC 3.4.21.31). uPA is a 411 amino acid residue protein consisting of three domains: the growth factor-like domain (aa 4-43), the kringle domain (aa 47-135) and the catalytic "B" chain (amino acids 144-411) The kringle domain appears to bind heparin. The growth factor-like domain bears some similarity to the structure of epidermal growth factor (EGF), and is thus referred to as an EGF-like domain. uPA is synthesized as a zymogen (pro-uPA or single chain uPA), and is activated by proteolytic cleavage by plasmin between Lys158 and Ile159. The two resulting chains are kept together by a disulphide bond.

A principal substrate for uPA is plasminogen which is converted by cell surface bound uPA to plasmin. uPA is highly specific to a single peptide linkage in plasminogen. Activated plasmin degrades components of the extracellular matrix (fibrin, fibronectin, laminin, and proteoglycans) and also activates matrix metalloproteases (MMPs) thus promoting the degradation of collagen. Therefore, cosmetic composition which provide benzylsulfonyl-D-Ser-L-hPhe-4-amidinobenzylamide, provide a potent selective inhibitor of the urokinase, and a potent plasmin inhibitor while not inhibiting serine proteases, including kallikrein 5, kallikrein 7, elastase, factor VII, factor X and tissue-type plasminogen activator (tPA).

Thus, benzylsulfonyl dipeptide derivatives and in particular benzylsulfonyl-Ser-hPhe-4-amidinobenzylamide, (formula (II)) are important and valuable compounds for the use in the field of personal care application.

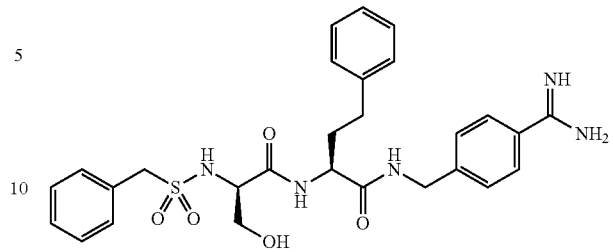

Formula (II)

When a compound according to formula (I) is manufactured according to procedures as described in WO 2001/096286, WO 2003/076391, or as published by A. Schweinitz et al. in JBC 2004, Vol 279 (32), p 33613-3622, the yield of the resulting product is very limited because of the surprisingly low solubility of said compounds of formula (I), thereby drastically increasing the cost of production of said compounds. The poor yield of the process of the prior art is demonstrated in comparative examples. Furthermore; the above described processes of the prior art include an ionic exchange chromatographic step which is not convenient for industrial scale production with poorly soluble compounds.

Therefore the goal of the present invention was to find an improved process for coupling an amino acid derivative of formula (III), herein designated as benzylsulfonyl-Ser (tBu)-OH with a compound of formula (IV) herein designated as X-4-amidinobenzylamide thereby leading to the compound of formula (I) with an excellent yield, a minimal amount of side products, fewer steps than the processes of the prior art, thereby leading to a significant reduction of the manufacturing cost.

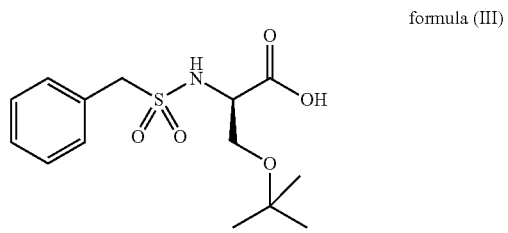

formula (III)

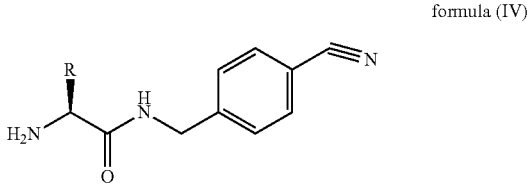

formula (IV)

wherein R is a $C_1$ to $C_6$ linear or branched aliphatic hydrocarbon chain optionally substituted with a $C_6$ to $C_{10}$ aromatic group.

DETAILED DESCRIPTION OF THE INVENTION

Surprisingly, the present inventors found that a compound of formula (I) can be manufactured with a very high yield, high purity, with impurity profile which does not trigger any safety concern for personal care applications, and in fewer steps.

Therefore the present invention relates to a process for the production of a compound of formula (I) or a salt thereof,

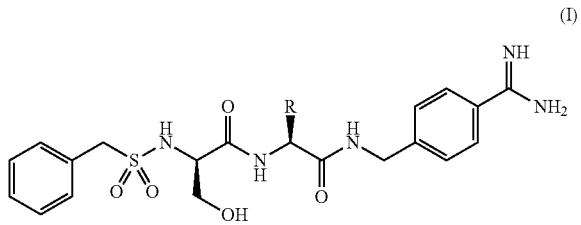

comprising the steps of
i) coupling by condensation a compound of formula (III) with a compound of formula (IV), or a salt thereof,

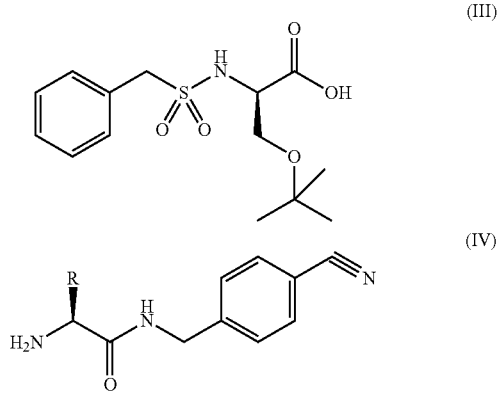

ii) converting the nitrile function to hydroxy amidine,
iii) removing the tert-butyl ether protecting group with a strong acid in the presence of a scavenger, at a temperature of −10 to 30° C.,
iv) reducing the hydroxyl amidine or protected hydroxy amidine function to the amidine, leading to the product of formula (I),
wherein,
R is a $C_1$ to $C_6$ linear or branched aliphatic hydrocarbon chain optionally substituted with a $C_6$ to $C_{10}$ aromatic group.

In all the embodiments of the present invention, the compound of formula (I) is characterized in that R is a $C_1$ to $C_6$ linear or branched aliphatic hydrocarbon chain optionally substituted with a $C_6$ to $C_{10}$ aromatic group, preferably, R is $C_1$ to $C_3$ linear aliphatic hydrocarbon chain substituted with a $C_6$ to $C_8$ aromatic group, more preferably, R is —$CH_2$—$CH_2$—$C_6H_5$ meaning that the compound of formula (I) is benzylsulfonyl-Ser-hPhe-4-amidinobenzylamide (formula (II)). Moreover, the compound of formula (I) can be in any stereo chemical configuration, but the preferred configuration is the compound of formula (I) resulting from the condensation of benzylsulfonyl-D-Ser (tBu)-OH and L-X-4-cyanobenzylamide thus leading to benzylsulfonyl-D-Ser-L-X-4-amidinobenzylamide. Most preferred compound of formula (I) is the compound of formula (II) resulting from the condensation of benzylsulfonyl-D-Ser (tBu)-OH and L-homoPhe-4-cyanobenzylamide thus leading to benzylsulfonyl-D-Ser-L-homoPhe-4-amidinobenzylamide. HomoPhe and hPhe are used interchangeably to mean homophenylalanine (CAS 943-73-7).

The compounds of formula (I) are as a rule present as salts, preferably with mineral acids, preferably as hydrochlorides or as salts with suitable organic acids or sulfates. Preferred organic acids salts for the compounds of formula (I) are selected from acetic acid, formic acid, methylsulfonic acid, succinic acid, malic acid, trifluoroacetic acid, most preferred being acetate salts.

Coupling by Condensation Step: Step i)
The compound of formula (III) can in principle be prepared by methods know to the person skilled in the art as described in "The Practice of Peptide Synthesis", $2^{nd}$ Ed., M. Bodanzky & A. Bodanzky, Springer-Verlag).

The compound of formula (IV) can in principle be prepared by methods know to the person skilled in the art as described in "The Practice of Peptide Synthesis", $2^{nd}$ Ed., M. Bodanzky & A. Bodanzky, Springer-Verlag). The compound of formula (IV) is added as a salt, preferably as a HCl salt.

For the process according to the present invention, the condensation of step i) can be carried out by any conventional coupling reaction known to the person skilled in the art. Preferably, step i) is carried out in an organic solvent selected from acetonitrile, THF, and DMF or mixtures thereof, with at least one peptide coupling reagent selected from 2-MBT (2-mercaptobenzothiazole), BOP ((Benzotriazol-1-yloxy)tris(dimethylamino) phosphonium hexafluorophosphate; CAS Nr.: 56602-33-6), TBTU (O-(Benzotriazol-1-yl)-N,N,N',N'-tetramethyluronium tetrafluoroborate CAS Nr.: 125700-67-6), HBTU (N,N,N',N'-Tetramethyl-O-(1H-benzotriazol-1-yl)uronium hexafluorophosphate, O-(Benzotriazol-1-yl)-N,N,N',N'-tetramethyluronium hexafluorophosphate; CAS Nr: 94790-37-1), and COMU (1-Cyano-2-ethoxy-2-oxoethylidenaminooxy)dimethylamino-morpholino-carbenium hexafluorophosphate; CAS Nr: 1075198-30-9). More preferably, the organic solvent is a mixture of acetonitrile/THF in a 1/1 ratio, and the peptide coupling reagent is TBTU.

Reaction is usually carried out for 6 to 18 hours at a temperature of 4° C. to 25° C.

Nitrile Conversion Step: Step ii)
For the process according to the present invention, the conversion of step ii) is carried out by methods known in the art. Preferably, it is performed with hydroxylamine in the presence of a solvent or solvent mixture such as DMF, THF, methanol, ethanol, or acetonitrile. Most preferred solvent is methanol. Most preferred reaction time is 6 to 7 hours and preferred reaction temperature is between 60° C. and 65° C.

Removal of the tert-butyl ether Protecting Group: Step iii)
For the process according to the present invention, the deprotection of step iii) is carried out with a strong acid in the presence of a scavenger at a temperature of −10° to 30° C. It is essential to perform step iii) at a low temperature (between −10° C. and 30° C.) in order to prevent migration of the t-butyl carbocation to the amidoxime function which would lead to impurities in the final product.

Preferably according to the present invention, the strong acid used in step iii) is selected from halogenated organic acids, preferably it is trifluoroacetic acid (TFA).

Preferably, step iii) is performed at temperature of 0 to 20° C., more preferably, 2 to 10° C., even more preferably, 4 to 8° C.

Step iii) is carried out in the presence of a scavenger i.e.: a nucleophilic scavenger such as triisopropylsilane (TIPS) or triethyl silane (TES) or an organic sulphur-containing compound, preferably a thiol, such as ethanedithiol, thioanisole, thiophenol and 2,2'-(ethylenedioxy)diethanethiol (DODT), more preferably an alkyl thiol, such as ethane dithiol or dodecanethiol (DODS). Even more preferably, step iii) is performed with dodecanethiol (DODS) and trifluoroacetic acid (TFA) in a ratio of 70/30 to 95/5 (v/v) of TFA/DODS.

Reduction of the hydroxylamidine: Step iv)

For the process according to the present invention, the reduction of step iv) which reduces the hydroxyl amidine or protected hydroxy amidine function to the amidine function is performed according to standard reduction process, and is best performed in the presence of a metal catalyst by hydrogenation or transfer hydrogenation.

Usually the hydrogenation is carried out by using $H_2$-gas. It is possible, and preferred, to use pure $H_2$-gas, but it would also be possible to use a gas mixture which comprises $H_2$. Therefore the present invention relates to a process as described above wherein the hydrogenation is carried out by (pure) $H_2$-gas.

The hydrogenation is usually carried out under pressure. All pressures stated below mean relative pressure above atmospheric pressure. Therefore, the present invention relates to a process wherein the hydrogenation is performed under a pressure above atmospheric pressure of at least 0.1 bar. Preferably, a pressure of not more than 50 bar is used. A preferred range for the pressure according to the present invention is 0.1-10 bar, more preferably 0.1-5 bar. Moreover, the hydrogenation is usually carried out in a vessel, which is suitable to enduring the pressure.

The hydrogenation is usually carried out at temperature from 20° C. to 120° C. Preferably, it is carried out at a temperature from 25 to 80° C., most preferably, from 30° C. to 50° C. Therefore the present invention relates to a process as described above wherein, the hydrogenation is carried out at a temperature of 20° C. to 120° C., more preferably 25° C. to 80° C., most preferably, 30° C. to 50° C.

The hydrogenation according to step iv) of the present invention is performed by hydrogenation with a nickel or palladium catalyst. Preferably, the catalyst is a heterogeneous catalyst such as a palladium on carbon or a nickel alloy catalyst. Such catalysts are commercially available for example under the trade name 5% palladium on carbon Type 39 (or equivalent) from Johnson Matthey or 5% palladium on carbon E 101 N/D (or equivalent) from Evonik or Nickel catalyst MC113 (or equivalent) from Evonik or nickel catalyst A5000 (or equivalent) from Johnson Matthey. The present hydrogenation reaction is however not restricted to the catalysts listed above.

In the process according to the present invention, the catalyst can be reused for further hydrogenation, and can also easily be recycled. Usually the catalyst can be used without further treatment. So it is possible to run the hydrogenation batchwise or continuously.

The ratio (related to the weight) of hydroxy amidine obtained in step iii) to the catalyst in the hydrogenation reaction mixture is usually at least 5:1.

A solvent or a mixture of solvents is used for the hydrogenation. Suitable solvents are esters; ethers; alcohols; amides; nitriles; acids and water. Preferably, solvents used are liquid under normal conditions, which allow an easy handling. Preferred solvents are mixtures comprising N,N,-dimethylformamide (DMF), ethanol (EtOH), water, acetic acid (HOAc), tetrahydrofuran (THF) or acetonitrile (ACN).

In a preferred embodiment, step iv) is carried out in the presence of a palladium catalyst in a solvent mixture comprising either THF 30-80 Wt. %, HOAc 5-50 Wt. %, DMF 0-30 Wt. % water 0-40 Wt. %; or ACN 30-80 Wt. %, HOAc 5-50 Wt. %, water 0-40 Wt. %; or EtOH 30-80 Wt. %, HOAc 5-50 Wt. %, DMF 1-30 Wt. % and water 0-40 Wt. %.

More preferably, the solvent mixture comprises EtOH 30-80 Wt. %, HOAc 5-50 Wt. %, DMF 1-30 Wt. % and water 1-40 Wt. %.

Alternatively, step iv) is carried out in the presence of a nickel catalyst in a solvent mixture comprising either HOAc 50-95 Wt. %, water 5-50 Wt. %; or THF 50-95 Wt. %, water 5-50 Wt. %; or THF 30-70 wt. %, DMF 20-40 Wt. %, water 10-30 Wt. %.

Most preferred embodiment is when step iv) is carried out in the presence of a nickel catalyst in a solvent mixture comprising HOAc 50-95 Wt. %, water 5-50 Wt. %.

Most preferred process according to the present invention is a process for the production of benzylsulfonyl-D-Ser-L-hPhe-4-amidinobenzylamide or a salt thereof comprising the steps of i) coupling by condensation a compound of formula (III) with a compound of formula (IV), or a salt thereof,

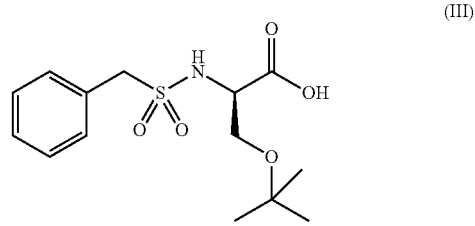

(III)

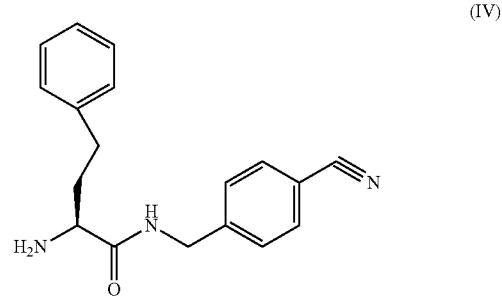

(IV)

ii) converting the nitrile function to hydroxy amidine, iii) removing the tert-butyl ether protecting group with a strong acid in the presence of a scavenger, at a temperature of 2 to 10° C., iv) reducing the hydroxyl amidine or protected hydroxy amidine function to the amidine, leading to the product benzylsulfonyl-D-Ser-L-hPhe-4-amidinobenzylamide, wherein, the condensation of step i) is carried out for 6 to 18 h at a temperature of 4° C.-25° C. in an organic solvent which is a mixture acetonitrile/THF in a 1/1 ratio, the peptide coupling reagent is TBTU, step ii) is performed with hydroxylamide in the presence of methanol for 6 to 7 h at 60 to 65° C., step iii) is performed with trifluoroacetic acid (TFA) in the presence of dodecanethiol (DODS) in a ratio TFA/DODS between 70/30 to 95/5 (w/w), and step iv) is performed by hydrogenation with a nickel catalyst in a solvent mixture comprising HOAc 50-95 Wt. %, water 5-50 Wt. %

The following examples serve to illustrate the invention. If not otherwise stated all parts given are related to the weight and the temperature is given in degree Celsius (° C.).

EXAMPLES

Example 1 Production of-benzylsulfonyl-D-Ser-L-hPhe-4-amidinobenzylamide 33.3 g (90 mmol) of H-homoPhe-NHBzl(4CN)×HCl (compound of formula IV) was dissolved in 165 ml of a 1:1 mixture of acetonitrile and THF. 11.6 g (90 mmol) of DIPEA was added and stirred for 2 min, then the remainder of DIPEA, 23.7 g (183.6 mmol), followed by 28.9 g (91.8 mmol, 1.02 eq) of PMS-D-Ser(tBu)-OH (compound of formula III) dissolved in 165 ml of THF. The solution was chilled to 4° C. and 29.5 g of TBTU (91.8 mmol) was added as solid. The lightly turbid suspension was stirred at 4° C. for 1 h, allowed to warm to RT and stirred overnight.

The solvent was evaporated and the residue dissolved in 500 ml of EtOAc and extracted with 3 portions of 125 ml of 5% $Na_2CO_3$, 3 portions of 125 ml of 10% citric acid and once with saturated NaCl-solution. The organic phase was dried over $Na_2SO_4$, filtered and the solvent evaporated on a rotary evaporator at 40° C. whereby the product started to crystallize. The crude crystals were suspended in 470 ml of 2-propanol and heated to reflux whereby a clear solution was obtained. After allowing to cool to RT and stirring overnight, the crystals were filtered off and washed with 3 portions of 40 ml of ice-cold 2-propanol. A $2^{nd}$ crop of crystals was obtained and after drying of the crystals in a vacuum drying chamber overnight at 40° C./<1 mbar, a total of 40.9 g (77% yield) of off-white crystals were obtained. UPLC/ESI-MS: 99.9% (216 nm). ESI-MS (M+H theo: 591.3, found: 591.5).

39.6 g (67 mmol) of the nitrile derivative resulting from the coupling of the 2 building blocks was suspended in 410 ml of methanol, 13.3 g (201 mmol, 3 eq) of aqueous 50% hydroxylamine solution was added and the suspension heated to reflux (65° C.) whereby a clear solution was obtained within 5 min. The product crystallized out as a heavy solid and 90 ml of methanol was added to facilitate mixing. The solution was allowed to cool to RT and stirred overnight. Colorless needles were filtered off and washed with 2 portions of 40 ml of methanol. After recrystallization of the mother liquor and drying in a vacuum drying chamber for 3 days at 40° C./<1 mbar, 41 g (yield: 98%) of colorless needles were obtained. UPLC—99.9%, ESI-MS (M+H theo: 624.3, found: 624.5).

Step iii) and Step iv) Reaction with a Nickel Catalyst 19.5 g (31 mmol) of pre-chilled (4° C.) intermediate from step ii) of the process according the present invention, was dissolved in a pre-chilled solution (4° C.) of 108 ml of TFA and 9 ml DODS (38 mmol) under a stream of argon. The reaction mixture was stirred for 1 h at 4° C., warmed to 8° C. and stirred for a total of 15 h. After monitoring the reaction with UPLC to ensure complete deprotection and maximum suppression of by-product formation, the crude product was precipitated by dropwise addition to 1200 ml of diethylether at RT. After stirring for 1 h at RT, the product was filtered off and dried in a vacuum drying chamber for one day at 40° C./<1 mbar. A total of 20.8 g of crude product was obtained. The crude solid was dissolved in 200 ml THF and precipitated in a $NaHCO_3$-solution. After filtration and drying, the obtained solid was dissolved in 200 ml of acetic acid and precipitated in 1200 ml of diethylether. 14.6 g (82.2%) of an off-white granular solid was obtained. UPLC—98.5%, ESI-MS (M+H, theo: 568.2, found: 568.5). (See Table I, ID 10a and 10b)

19.5 g (34.4 mol) of intermediate from step iii) according to example 2 above, was dissolved in 140 ml of acetic acid and water (8/2). 1.95 g of activated charcoal was added and the suspension stirred for 30 min at RT and then hydrogenated with 2.35 g of Raney-Ni at 0.5 bar and 30° C. for 7 h. The catalyst and activated charcoal were filtered off, washed with water and the solvent evaporated. The residue was dissolved in 220 ml of 8/2 of THF/water at 40° C. The THF was evaporated and the product allowed to crystallize. After filtration and thorough washing with water, the product was dried in a vacuum drying chamber for 3 days at 40° C./<1 mbar. 18.8 g (89.2%) of an off-white solid was obtained. UPLC—97.3%, ESI-MS (M+H, theo: 552.2, found: 552). (See table II)

Example 2: Step iv) Reaction with a Palladium Catalyst 1.8 g (3.2 mol) of intermediate from step iii) according to example 1 above, was dissolved in 10 ml of EtOH/DMF/acetic acid/water (70/20/5/5). 180 mg of activated charcoal was added and the suspension stirred for 30 min at RT and hydrogenated with 360 mg of Pd/C at 8 bar and 50° C. for 1 d. Another 180 mg of catalyst was added and after 2 d at 8 bar and 50° C., the catalyst was filtered off, washed with water and the solvent evaporated. The residue was dissolved in 25 ml of 8/2 of THF/water at 40° C. The THF was evaporated and the product allowed to crystallize. After filtration and thorough washing with water, the product was dried in a vacuum drying chamber for 3 days at 40° C./<1 mbar. 1.66 g (85%) of an off-white solid was obtained. UPLC—97.5%, ESI-MS (M+H, theo: 552.2, found: 552.3). (See Table II, row 4)

Example 3: Optimization of Step iii)

Carrying out the deprotection (step iii)) solely in TFA at room temperature generates a large amount of side product (See reaction ID 1 lane 1 in Table I). The addition of a scavenger such as DODT, TES, TIPS and/or water, suppresses the formation of side product to a certain extent at higher temperatures (See reaction ID 2-8 in Table I). The optimal cleavage of t-butyl protecting group conversion with least amount of side product formation was surprisingly found to be at 4 to 8° C. over a duration of 15 hours (See reaction ID 9a-10b in Table I).

Table I: TFA is trifluoroacetic acid, DODT is 3,6-dioxa-1,8-octanedithiol, DODS is 1-dodecanethiol, TES is triethylsilane, TIPS is triisopropylsilane, W is water, DCM is dichloromethane, RT is room temperature, product of step iii) and educt product of step ii) are shown below:

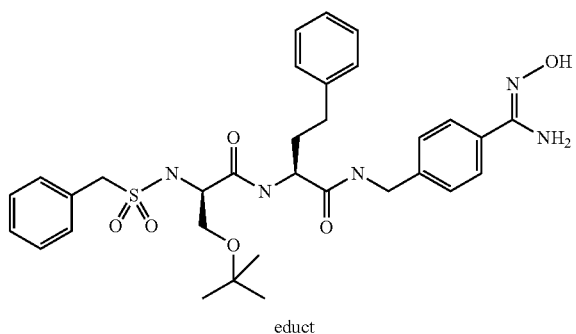

educt

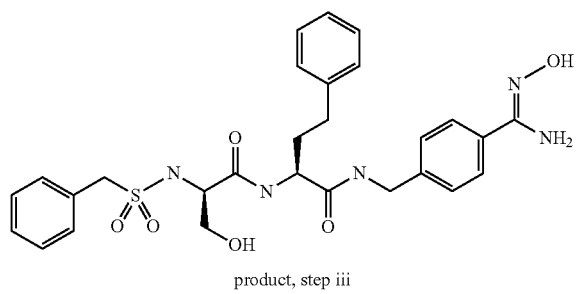

product, step iii

TABLE I

| ID | Solvent used | Sol. ratio | Time (h) | temp. (° C.) | Product (%) | Educt (%) | Impurity (%) |
|---|---|---|---|---|---|---|---|
| 1 | TFA | >99% | 1 | RT | 57.9 | 13.9 | 9.4 |
| 2 | TFA/DODT | 95/5 | 3 | 40 | 91.7 | 0.2 | 6.9 |
| 3 | TFA/DODT | 95/5 | 1 | 60 | 80.9 | <0.1 | 18.2 |
| 4 | TFA/TES/DODS/W | 85/5/5/5 | 22 | RT | 89.2 | 0.4 | 9.4 |
| 5 | TFA/TIPS/DCM | 94/1/5 | 3 | RT | 95.5 | <0.1 | 3.8 |
| 6 | TFA/W | 95/5 | 3 | 30 | 88.1 | 0.3 | 11.3 |
| 7 | TFA/W | 80/20 | 8 | 8 | 18.9 | 81.1 | <0.1 |
| 8 | TFA/W | 95/5 | 37 | 8 | 94.9 | 0.2 | 4.8 |
| 9a | TFA/DODS | 87/13 | 3 | 4 | 81.7 | 18.3 | <0.1 |
| 9b | TFA/DODS | 87/13 | 16 | 7 | 99.5 | <0.1 | 0.5 |
| 10a | TFA/DODS | 92/8 | 1 | 4 | 60.6 | 37.8 | 0.5 |
| 10b | TFA/DODS | 92/8 | 15 | 8 | 98.5 | 0.2 | 1.1 |

Example 4: Optimization of Step iv)

Educt 1 (see below) containing a Ser(Bzl) was hydrogenated using both catalysts. Although the expected reduction took place, surprisingly, the benzyl ether group was not deprotected even at higher temperatures and pressures, only product A was obtained.

Using educt 2 (see below) produced product B, which would have undergo a further 2 steps, a deprotection and an ion exchange step, to produce the desired product (formula II) in a total of 10 synthetic steps.

The hydrogenation of educt 3 (see below) in the presence of a palladium catalyst produced the desired product in various solvent mixtures and under relatively high pressure and moderate temperatures but required a duration of 2-3 days (example 2). In the presence of a nickel catalyst in various solvent mixtures, the reduction was surprisingly much faster and the desired product C, was obtained within a much shorter reaction time depending on the solvent mixture used. The total number of steps required to synthesize the product was therefore reduced from 10 to 8, which led to a significant reduction in production time and manufacturing cost (example 1).

Row 3 of Table II shows the process conditions according to the prior art. It shows that 10 synthesis steps were required to reach the final product.

Table II: EtOH is ethanol, DMF is dimethylformamide, HOAc is acetic acid, W is water, THF is tetrahydrofurane, ACN is acetonitrile. Na means that final product has not been produced.

Educt 1 and Product A are the following:

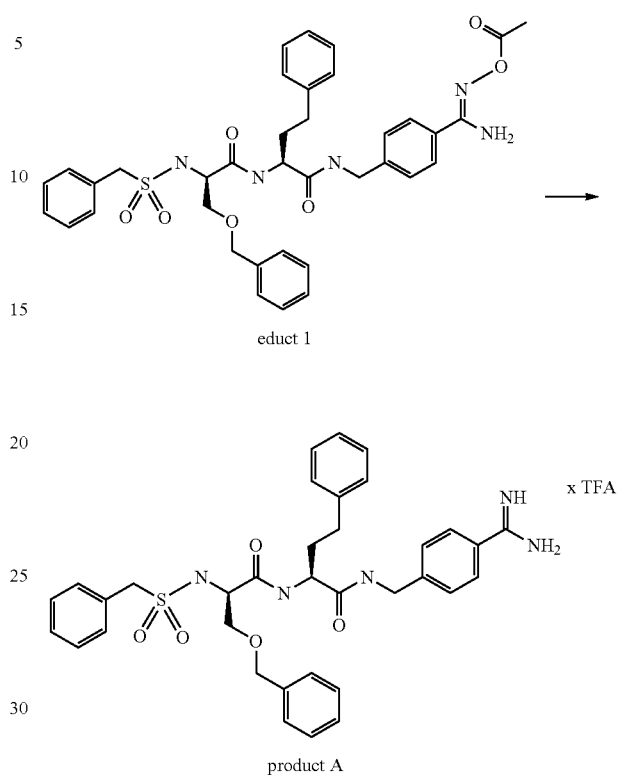

Educt 2 and Product B are the following:

Educt 3 and Product C are the following:

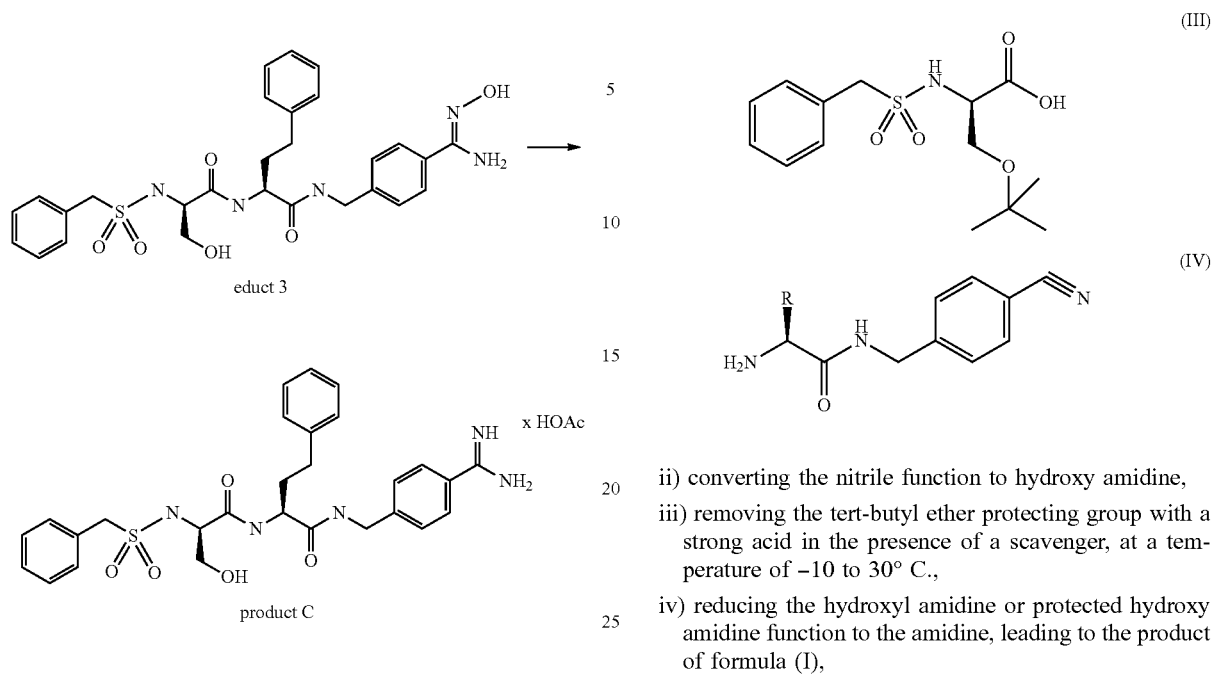

educt 3 product C ii) converting the nitrile function to hydroxy amidine,
iii) removing the tert-butyl ether protecting group with a strong acid in the presence of a scavenger, at a temperature of −10 to 30° C.,
iv) reducing the hydroxyl amidine or protected hydroxy amidine function to the amidine, leading to the product of formula (I),

TABLE II

| Educt | Catalyst | Pressure (bar) | Temp. (° C.) | time (h) | solvent | Solvent ratio | Product | Product (%) | Educt (%) | Nr. of steps |
|---|---|---|---|---|---|---|---|---|---|---|
| 1 | Pd/C | 20 | 50 | 16 | EtOH/DMF/HOAc/W | 70/20/5/5 | A | 95 | <0.1 | na |
| 1 | Raney/Ni | 10 | 50 | 15 | EtOH/W | 80/20 | A | 95 | <0.1 | na |
| 2 | Pd/C | 1 | 30 | 15 | DMF/HOAc/W | 80/10/10 | B | 95 | <0.1 | 10 |
| 3 | Pd/C | 8 | 50 | 48 | EtOH/DMF/HOAc/W | 70/20/5/5 | C | 98 | <0.1 | 8 |
| 3 | Pd/C | 8 | 50 | 48 | THF/W/HOAc | 34/33/33 | C | 99.5 | 0.5 | 8 |
| 3 | Pd/C | 8 | 50 | 48 | ACN/W/HOAc | 34/33/33 | C | 98.3 | 1.7 | 8 |
| 3 | Pd/C | 8 | 50 | 72 | THF/DMF/HOAc | 40/20/20 | C | 97 | 3 | 8 |
| 3 | Pd/C | 8 | 50 | 72 | THF/W/HOAc | 70/20/10 | C | 94 | 6 | 8 |
| 3 | Pd/C | 8 | 50 | 72 | THF/DMF/HOAc/W | 40/40/10/10 | C | 99.2 | 0.8 | 8 |
| 3 | Raney/Ni | 1 | 16 | 16 | THF/W | 80/20 | C | 98 | <0.1 | 8 |
| 3 | Raney/Ni | 0.45 | 18 | 18 | THF/W | 80/20 | C | 99.4 | <0.1 | 8 |
| 3 | Raney/Ni | 0.45 | 46 | 46 | THF/DMF/W | 48/34/18 | C | 97.5 | <0.1 | 8 |
| 3 | Raney/Ni | 0.5 | 7 | 7 | HOAc/W | 80/20 | C | 98.6 | <0.1 | 8 |

The invention claimed is:

1. A process for the production of a compound of formula (I) or a salt thereof,

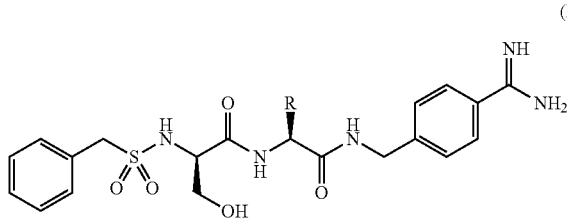

comprising the steps of
i) coupling by condensation a compound of formula (III) with a compound of formula (IV), or a salt thereof, wherein,
R is a $C_1$ to $C_6$ linear or branched aliphatic hydrocarbon chain optionally substituted with a $C_6$ to $C_{10}$ aromatic group.

2. Process according to claim 1, wherein the condensation of step i) is carried out in an organic solvent selected from acetonitrile, THF, and DMF or mixtures thereof, with at least one peptide coupling reagent selected from 2-MBT, BOP, TBTU, HBTU, and COMU.

3. Process according to claim 1, wherein the organic solvent used in step i) is a mixture acetonitrile/THF in a 1/1 ratio, and the peptide coupling reagent is TBTU.

4. Process according to claim 1, wherein step ii) is carried out with hydroxylamine in the presence of a solvent or solvent mixture selected from DMF, THF, acetonitrile, ethanol and methanol.

5. Process according to claim 1, wherein the strong acid in step iii) is selected from halogenated organic acids, and the scavenger is nucleophilic.

6. Process according to claim 1, wherein step iii) is performed at a temperature of 0 to 20° C.

7. Process according to claim 1, wherein step iv) is performed in the presence of a metal catalyst by hydrogenation or transfer hydrogenation.

8. Process according to claim 1, wherein step iv) is performed by hydrogenation with a nickel or palladium catalyst.

9. Process according to claim 1, wherein step iv) is carried out batch-wise or continuously.

10. Process according to claim 1, wherein step iv) is carried out in a solvent or solvent mixture containing at least one solvent chosen from the group consisting of esters; ethers; alcohols, amides, nitriles, acids and water.

11. Process according to claim 1, wherein step iv) is carried out with a palladium catalyst in a solvent mixture comprising either THF 30-80 Wt. %, HOAc 5-50 Wt. %, DMF 0-30 Wt. % water 0-40 Wt. %; or ACN 30-80 Wt. %, HOAc 5-50 Wt. %, water 0-40 Wt. %; or EtOH 30-80 Wt. %, HOAc 5-50 Wt. %, DMF 1-30 Wt. % and water 0-40 Wt. %, or with a nickel catalyst in a solvent mixture comprising either HOAc 50-95 Wt. %, water 5-50 Wt. %; or THF 50-95 Wt. %, water 5-50 Wt. %; or THF 30-70 wt. %, DMF 20-40 Wt. %, water 10-30 Wt. %.

12. Process according to claim 1, wherein step iv) is carried out with a nickel catalyst in a solvent mixture comprising either HOAc 50-95 Wt. %, water 5-50 Wt. %; or THF 50-95 Wt. %, water 5-50 Wt. %; or THF 30-70 wt. %, DMF 20-40 Wt. %, water 10-30 Wt. %.

13. Process according to claim 1, wherein step iv) is carried out under pressure of at least 0.1 bar using $H_2$ gas or a gas mixture comprising $H_2$.

14. Process according to claim 1, wherein step iv) is carried out at temperature from 20° C. to 120° C.

15. Process according to claim 1, wherein R is —$CH_2$—$CH_2$—$C_6H_5$.

16. Process according to claim 1, wherein step iii) is performed at a temperature of 2 to 10° C.

* * * * *